(12) United States Patent
Koseki et al.

(10) Patent No.: US 12,351,787 B2
(45) Date of Patent: Jul. 8, 2025

(54) CULTURE CONTAINER, CULTURE METHOD, AND TRANSPORTATION METHOD

(71) Applicant: TOYO SEIKAN GROUP HOLDINGS, LTD., Tokyo (JP)

(72) Inventors: Osamu Koseki, Kanagawa (JP); Satoshi Tanaka, Kanagawa (JP)

(73) Assignee: TOYO SEIKAN GROUP HOLDINGS, LTD., Tokyo (JP)

( * ) Notice: Subject to any disclaimer, the term of this patent is extended or adjusted under 35 U.S.C. 154(b) by 727 days.

(21) Appl. No.: 17/241,813

(22) Filed: Apr. 27, 2021

(65) Prior Publication Data

US 2021/0246405 A1 Aug. 12, 2021

Related U.S. Application Data

(63) Continuation of application No. PCT/JP2019/041436, filed on Oct. 23, 2019.

(30) Foreign Application Priority Data

Oct. 30, 2018 (JP) .................. 2018-204506

(51) Int. Cl.
*C12M 1/32* (2006.01)
*C12M 1/12* (2006.01)
*C12M 1/34* (2006.01)

(52) U.S. Cl.
CPC ............ *C12M 23/12* (2013.01); *C12M 25/06* (2013.01); *C12M 41/32* (2013.01)

(58) Field of Classification Search
CPC .............................. C12M 23/12; C12M 25/06
(Continued)

(56) References Cited

U.S. PATENT DOCUMENTS 4,657,867 A * 4/1987 Guhl ..................... C12M 23/38
435/305.3
2017/0067006 A1 3/2017 Obi et al.

FOREIGN PATENT DOCUMENTS

CN 108520866 A 9/2018
EP 0183973 A1 6/1986
(Continued)

OTHER PUBLICATIONS

JP-2009011260-A Machine English Translation (Year: 2009).*
(Continued)

*Primary Examiner* — Michael L Hobbs
*Assistant Examiner* — Lenora A Abel
(74) *Attorney, Agent, or Firm* — Nakanishi IP Associates, LLC

(57) ABSTRACT

In a culture container including a plurality of recesses for culturing a culture target, such as spheres, a liquid substance can flow between the recesses and the movement of the culture target between the recesses can be prevented. A culture container includes a plurality of recesses for accommodating a culture target, the culture container including a container body having a first surface in which the recesses are formed, and a top plate having a second surface facing the first surface, protrusion portions and/or channel portions being provided on a side of the first surface and/or a side of the second surface, the container body being in contact with a part of the top plate to form a channel between the container body and the top plate, and a width of the channel being smaller than a minimum diameter of the culture target.

7 Claims, 7 Drawing Sheets

(58) Field of Classification Search
USPC .................................................. 435/305.2
See application file for complete search history.

(56) References Cited

FOREIGN PATENT DOCUMENTS

| EP | 3109313 A1 | 12/2016 | | |
|---|---|---|---|---|
| JP | S61-108372 A | 5/1986 | | |
| JP | 2009011260 A | * | 1/2009 | ............ C12M 23/04 |
| JP | 2015073520 A | * | 4/2015 | |
| JP | 2018-000050 A | 1/2018 | | |
| JP | 2018-108032 A | 7/2018 | | |
| WO | 2015/198866 A1 | 12/2015 | | |
| WO | 2017/057126 A1 | 4/2017 | | |

OTHER PUBLICATIONS

JP-2015073520-A Machine English Translation (Year: 2015).*
International Search Report issued in PCT/JP2019/041436 mailed on Jan. 21, 2020 with English Translation (5 pages).
Office Action issued in Chinese Patent Application No. 201980071026.6, mailed on Jul. 1, 2023, with English Translation of Main Body Text (12 pages).
Extended European Search Report issued in European Patent Application No. 19878874.7, dated Jul. 15, 2022 (7 pages).
Office Action issued in Japanese Patent Application No. 2018-204506, mailed on Sep. 6, 2022, with English Translation (8 pages).

* cited by examiner

CULTURE CONTAINER, CULTURE METHOD, AND TRANSPORTATION METHOD

TECHNICAL FIELD

The present invention relates to a cell culture-related technique, in particular, relates to a technique of promoting the efficiency of sphere formation and the like.

BACKGROUND ART

In recent years, large amounts of adherent cells, such as stem cells including iPS cells and ES cells, are cultured not only by attaching cells to a culture container to grow, but also by using a method of culturing cells in a three-dimensional state closer to in vivo by forming spheres (spheroids, aggregates) and organoids using a culture container including a microwell plate etc., coated with a material having low adhesion to cells.

The mass culture of spheres using such a culture container had a problem that it was difficult to obtain spheres with a desired size and shape because the spheres popped out of the wells (recesses) and moved to other wells.

For example, when a medium was fed into a culture bag (bag-shaped culture container) including many wells on its culture surface in order to replace the medium, the spheres easily popped out of the wells and moved to other wells. It was thus necessary to extremely slow down the flow rate of the medium, and it was very difficult to replace the medium quickly. Therefore, this type of culture container was not suitable for long-term culture, which required frequent medium replacement.

In addition, in such a culture container, the spheres easily popped out of the wells only upon vibration, and it was thus not easy to move the culture container safely while culturing spheres.

CITATION LIST

Patent Literature

Patent Document 1: JP-A-2018-108032
Patent Document 2: JP-A-2018-50

SUMMARY OF INVENTION

Technical Problem

An example of techniques related to solutions of such problems is the culture vessel disclosed in Patent Document 1. The culture vessel includes a vessel main body including a bottom portion formed with a compartment, and a peripheral wall portion rising from an edge portion of the bottom portion; and a partition member disposed at a position opposed to the bottom portion; and at least a portion of the partition member is immersed in the culture liquid within the vessel main body. This can prevent the movement of spheres during movement of the culture vessel or replacement of the medium.

However, there was a problem that it was difficult to align the peripheral wall portion of the compartment with the partition member and to adjust the gap between the compartment and the partition member. In addition, the alignment and adjustment became more difficult when the bottom portion and the partition member were warped. For this reason, it was difficult to apply this culture vessel to a culture bag made of a flexible packaging material.

Another example is the cell culture container disclosed in Patent Document 2. The cell culture container includes a container body and a lid body capable of being freely taken in and out with respect to the bore of the container body, a plurality of crevices for containing cells are arranged in the bottom face of the bore, and the lid body is made of a liquid-permeable material with flexibility. In the condition that the lid body is immersed in culture medium, the under face of the lid body is formed so as to follow the bottom face. This makes it possible to confine spheres to a compartment.

However, it was also difficult to apply this cell culture container particularly to a culture bag made of a flexible packaging material because a gap was sometimes formed between the crevices and the lid body when the container body was warped. In addition, with this cell culture container, it was difficult to discharge the whole culture medium in the crevices, and it was not suitable for rapid medium replacement.

Then, as a result of extensive studies, the present inventors have succeeded in developing a culture container including a container body having a first surface in which recesses are formed, and a top plate having a second surface facing the first surface, protrusion portions and/or channel portions being provided on a side of the first surface and/or a side of the second surface, the container body and the top plate being partially in contact with each other to form a channel between the container body and the top plate, and the channel having a width smaller than the minimum diameter of a culture target, such as spheres; wherein a liquid substance, such as a medium, can flow between the number of recesses formed in the culture container, cells and debris smaller than the minimum diameter of the culture target can pass between the recesses, and the movement of spheres etc. between the recesses can be prevented.

Moreover, this culture container does not require the alignment of the recesses and the top plate, and can be easily realized as a closed-type culture bag made of a flexible packaging material. Furthermore, since spheres etc. do not move between the recesses even when the medium is replaced, this culture container can be suitably used for long-term culture.

The present invention was made in view of the above circumstances. An object of the present invention is to provide a culture container including a plurality of recesses for culturing a culture target, such as spheres, wherein a liquid substance can flow between the recesses and the movement of the culture target between the recesses can be prevented, and to also provide a culture method and a transportation method.

Solutions to Problem

In order to achieve the above object, the culture container of the present invention is a culture container including a plurality of recesses for accommodating a culture target, the culture container including a container body having a first surface in which the recesses are formed, and a top plate having a second surface facing the first surface, protrusion portions and/or channel portions being provided on a side of the first surface and/or a side of the second surface, the container body and the top plate being partially in contact with each other to form a channel between the container body and the top plate, and a width of the channel being smaller than a minimum diameter of the culture target.

Further, the culture container of the present invention is preferably configured such that top plate protrusion portions are provided on the second surface side, a width of the top plate protrusion portion is smaller than a width of an opening of the recess, a height of the top plate protrusion portion is smaller than the minimum diameter of the culture target, and the top plate protrusion portions are in contact with a part of the first surface to form a gap between the first surface and the second surface.

Moreover, the culture method of the present invention is a culture method using the above culture container, the method including inserting and removing a medium or a cleaning liquid through the channel formed between the container body and the top plate.

In addition, the transportation method of the present invention is a method for storing or transporting the culture target using the above culture container while accommodating the culture target in the recesses and filling the recesses and the channel formed between the container body and the top plate with a medium, a cleaning liquid, or a cell preservation liquid.

Advantageous Effects of Invention

According to the present invention, it is possible to provide a culture container including a plurality of recesses for culturing a culture target, such as spheres, wherein a liquid substance can flow between the recesses and the movement of the culture target between the recesses can be prevented, and to also provide a culture method and a transportation method.

DESCRIPTION OF EMBODIMENTS

Hereinafter, embodiments of the culture container, the culture method, and the transportation method according to the present invention will be described in detail. Note that the present invention is not limited to the specific contents of the following embodiments.

First Embodiment

Figure 1:
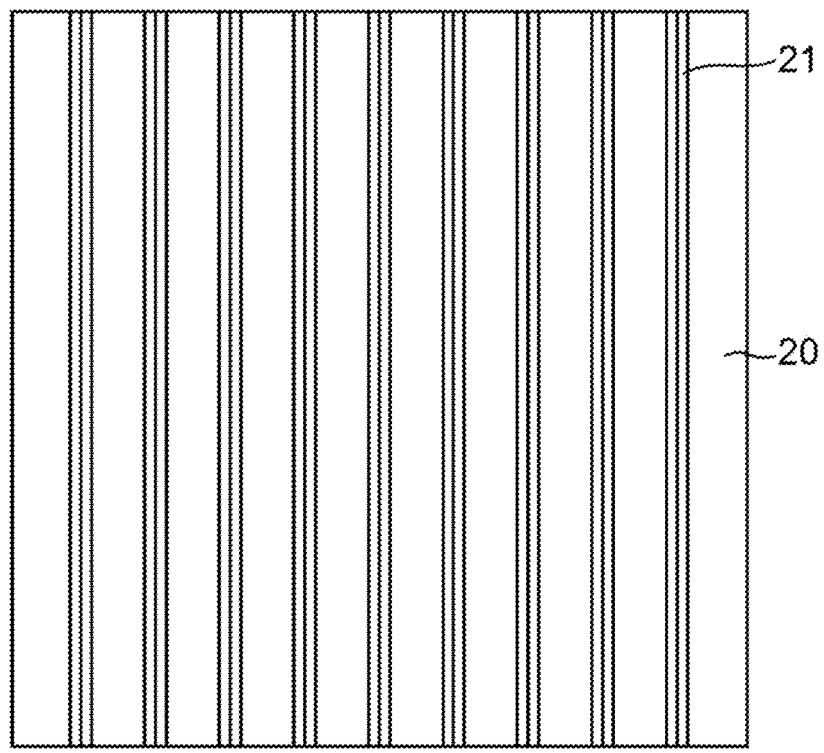
FIG. 1 shows schematic diagrams illustrating a top plate and a container body in a culture container according to a first embodiment of the present invention.
Figure 1:
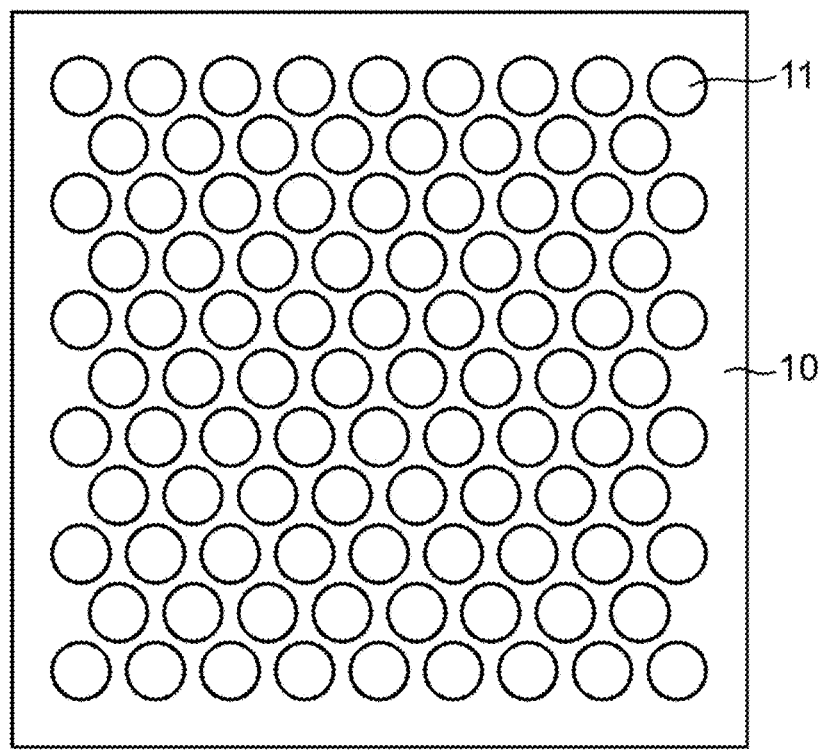
Figure 2:
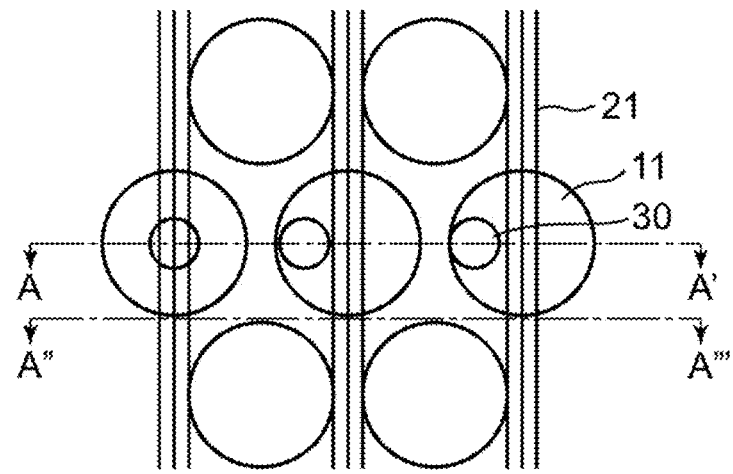
FIG. 2 shows a partially enlarged schematic plan view and cross-sectional views of the culture container according to the first embodiment of the present invention.
Figure 2:
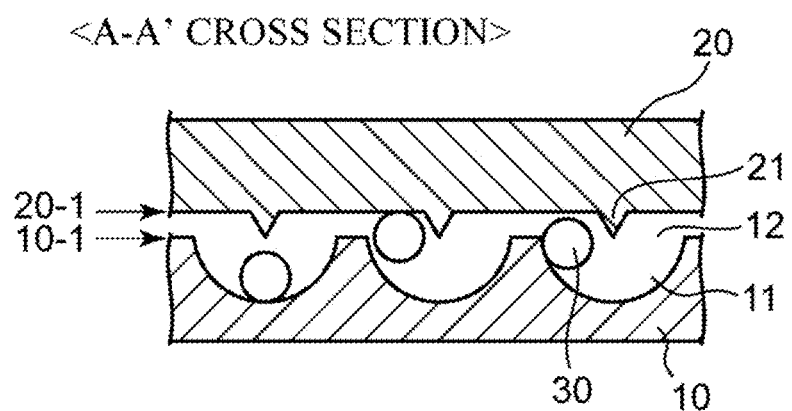
Figure 2:
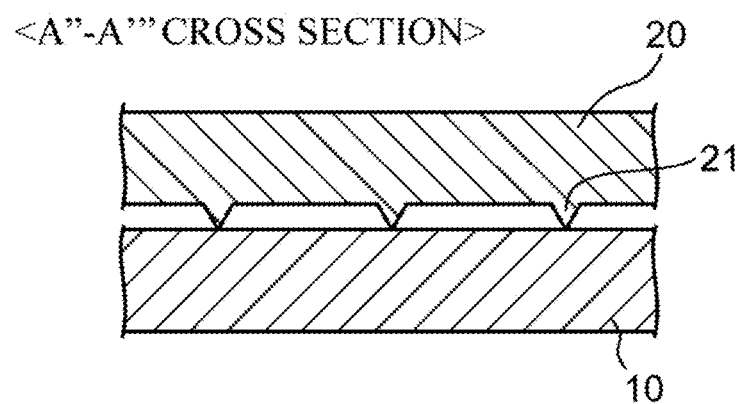

The culture container, the culture method, and the transportation method according to the first embodiment of the present invention will be described with reference to FIGS. 1 and 2. FIG. 1 shows schematic diagrams illustrating a top plate and a container body in the culture container according to the present embodiment, and FIG. 2 shows a partially enlarged schematic plan view and cross-sectional views of the culture container according to the present embodiment.

The culture container of the present embodiment is a culture container including a plurality of recesses for accommodating a culture target, and is formed by bonding a container body 10 and a top plate 20 as shown in FIG. 1 by heat sealing or the like.

The container body 10 has a first surface 10-1 in which openings 12 of recesses 11 are formed, and the first surface 10-1 and the surface that forms the side walls of the recesses 11 are used as a culture surface to configure the bottom of the culture container. The number of recesses 11 is not particularly limited.

The top plate 20 has a second surface 20-1 facing the first surface 10-1 of the container body 10.

Then, the first surface 10-1 of the container body 10 and the second surface 20-1 of the top plate 20 are disposed to face each other to form a culture container, and the container body 10 and the top plate 20 are partially in contact with each other to form a channel between the container body 10 and the top plate 20. The width of the channel is smaller than the minimum diameter of a culture target 30. The channel is formed by protrusion portions in the first and second embodiments, and is formed by channel portions in the third and fourth embodiments.

Specifically, the culture container of the present embodiment includes top plate protrusion portions 21 on the second surface 20-1 side of the top plate 20.

The width of the top plate protrusion portion 21 is smaller than the width of the opening 12 of the recess 11 of the container body 10, and the height of the top plate protrusion portion 21 is smaller than the minimum diameter of the culture target 30.

Then, the tips of the top plate protrusion portions 21 are in contact with a part of the first surface 10-1 of the container body 10 (other than regions corresponding to the openings 12) in contact with each to form a gap between the first surface 10-1 of the container body 10 and the second surface 20-1 of the top plate 20.

FIG. 2 shows a schematic plan view illustrating a state in which spheres as the culture target 30 are accommodated in part of such a culture container, an A-A' cross-sectional view, and an A"-A''' cross-sectional view.

In the A-A' cross-sectional view, the top plate protrusion portions 21 have an elongated triangular prism shape protruding from the second surface 20-1, and are arranged at regular intervals above all of the recesses; however, the shape and arrangement of the top plate protrusion portions 21 are not limited thereto. Various shapes and arrangements can be employed within the range in which a gap can be formed between the first surface 10-1 and the second surface 20-1.

That is, the top plate protrusion portions 21 can have, for example, a semicircular cylindrical shape protruding from the second surface 20-1, and can be arranged at random on the second surface 20-1.

The gap between the first surface 10-1 of the container body 10 and the second surface 20-1 of the top plate 20 is the same as the height of the top plate protrusion portion 21, and the height of the top plate protrusion portion 21 is smaller than the diameter of the culture target.

Therefore, the culture target cannot pass through the gap between the first surface 10-1 and the second surface 20-1, and can be retained in the recesses 11.

That is, even if a liquid substance, such as a medium, is fed through the gap between the first surface and the second surface, the culture target, such as spheres, can neither move from the recesses nor enter the neighboring recesses.

Therefore, the culture container of the present embodiment makes it possible to solve the conventional problem that it is difficult to obtain spheres with a desired size and shape.

Further, even if the flow rate of the medium is increased, the spheres do not pop out of the recesses or move to other recesses; thus, the medium can be easily inserted and removed to facilitate the replacement of the medium. In addition, the culture container can be easily moved while culturing spheres.

Furthermore, in the case of replacing the entire medium, the medium in the culture container can be easily inserted and removed through the gap between the first surface and the second surface by tilting or inverting the culture container. That is, the medium can be easily homogenized when inserted, and the medium can also be easily discharged. In addition, a cleaning liquid can also be easily inserted and removed in this manner.

Thus, the culture container of the present embodiment can keep the spheres in the recesses even when the culture container is tilted or inverted, which can facilitate the replacement of the medium.

The culture container of the present embodiment can also be used to clean the culture target.

That is, a cleaning liquid, such as a phosphate buffer, physiological saline, or a cell preservation liquid, is injected into the culture container, and the culture container is tilted or inverted to discharge the cleaning liquid from the culture container, whereby the culture target can be easily cleaned. In general sphere cleaning, the following operation was carried out several times: spheres were once collected and suspended in a container, such as a centrifuge tube, filled with a cleaning liquid, and after the spheres were settled, the supernatant in cleaning was removed. Since spheres have a tendency to aggregate when they come into contact with each other, it is necessary to carry out the cleaning operation in a short time. Conventional methods had a risk of aggregation of spheres in the worst case; however, this problem can be easily solved by the culture container of the present embodiment.

Moreover, the culture container of the present embodiment makes it possible to obtain culture targets in a state of being arranged in sections each including a plurality of recesses, and to obtain the culture targets with a uniform size depending on the recesses.

Furthermore, since it is possible to obtain culture targets in a state of being arranged in each section, the culture targets can be easily counted.

In addition, the culture container of the present embodiment also makes it possible to store or transport a culture target while accommodating the culture target in the recesses and filling the recesses and the channel formed between the container body and the top plate with a medium, a cleaning liquid, or a cell preservation liquid.

Thus, the culture container of the present embodiment is used to perform medium replacement, cleaning, transportation, etc., while filling the recesses and the channel formed between the container body and the top plate with a medium, a cleaning liquid, or the like. It is needless to say that the container body and the top plate do not have through holes or the like.

As the culture target 30 in the present embodiment, cells, body tissues, etc., can also be used, in addition to spheres. The culture target 30 also includes objects to be cleaned.

That is, when the width of the channel formed between the container body 10 and the top plate 20 is set to a value suitable for the size of the culture target 30, the culture container can be applied to the culture of various culture targets 30 and to the cleaning thereof.

Further, in the culture container of the present embodiment, the container body 10 and/or the top plate 20 can be made of a flexible packaging material, and can be configured as a culture bag.

That is, in the culture container of the present embodiment, the tips of the top plate protrusion portions 21 can be easily brought into contact with a part of the first surface of the container body 10 by pressing the top plate 20 against the container body 10, and the contact state can be maintained.

At this time, for example, the container body 10 can be pressed by the top plate 20 using a spring or a magnet, or by means of suction. It is possible to appropriately control the width of the channel formed between the container body 10 and the top plate 20.

Moreover, in the culture container of the present embodiment, the width of the channel formed between the container body 10 and the top plate 20 can be easily controlled by pressing the top plate 20 against the container body 10. Since the width of the top plate protrusion portion 21 is smaller than the width of the opening 12 of the recess 11, the top plate protrusion portions 21 may be positioned anywhere with respect to the recesses 11, which can eliminate the need for strict alignment of the container body 10 and the top plate 20.

Here, the size of single cells is about 6 μm to 15 μm, and many of them have a size of about 10 μm. One sphere can be formed by aggregation of about 300 to several thousands of single cells. The size of the thus-formed spheres is about 50 μm to 100 μm for small spheres, and about 200 μm to 300 μm for large spheres.

Accordingly, when the culture target is spheres, it is desirable in the culture container of the present embodiment to set the width (height of the top plate protrusion portion 21) of the channel (gap) formed between the container body 10 and the top plate 20 depending on the size of the desired spheres. For example, to form small spheres, the width of the channel is preferably set to about 10 μm, 20 μm, 30 μm, or 40 μm. Further, to form large spheres, the width of the channel is preferably set to about 50 μm, 60 μm, 70 μm, 80 μm, 90 μm, or 100 μm.

Moreover, when the culture target is single cells, it is preferable in the culture container of the present embodiment to set the width of the channel formed between the container body 10 and the top plate 20 to, for example, about 2 μm, 3 μm, 4 μm, or 5 μm.

Furthermore, when the culture target is a body tissue, it is desirable in the culture container of the present embodiment to set the width of the channel formed between the container body 10 and the top plate 20 depending on the size of the target body tissue.

In addition, in the culture container of the present embodiment, the recesses 11 of the container body 10 have a hemispherical shape in the examples of FIGS. 1 and 2, but are not limited thereto. Their shape may also be a conical shape, a truncated conical shape, a polygonal prism shape, a polygonal pyramid shape, a truncated polygonal shape, or the like.

As the materials of the container body 10 and the top plate 20 in the culture container of the present embodiment, polyolefin-based resins, such as polyethylene and polypropylene, can be suitably used. Examples thereof include polyethylene, ethylene-α-olefin copolymers, ethylene-vinyl acetate copolymers, ionomers using ethylene-acrylic acid or methacrylic acid copolymers and metal ions, and the like. Other examples include polyolefins, styrene-based elastomers, polyester-based thermoplastic elastomers, silicone-based thermoplastic elastomers, silicone resins, and the like. Still other examples include silicone rubber, flexible polyvinyl chloride resins, polybutadiene resins, ethylene-vinyl acetate copolymers, chlorinated polyethylene resins, polyurethane-based thermoplastic elastomers, polyester-based thermoplastic elastomers, silicone-based thermoplastic elastomers, styrene-based elastomers (e.g., SBS (styrene-butadiene-styrene), SIS (styrene-isoprene-styrene), SEBS (styrene-ethylene-butylene-styrene), and SEPS (styrene-ethylene-propylene-styrene)), polyolefin resins, fluorine-based resins, and the like.

The same applies to the materials of the top plate protrusion portions 21 and body protrusion portions 13b, described later, in the present embodiment.

Moreover, when the culture target 30 is spheres, in the culture container of the present embodiment, the first surface 10-1 and the surface that forms the side walls of the recesses 11 of the container body 10 are preferably subjected to low-adhesion surface coating so that the spheres and single cells do not adhere thereto. Specifically, it is preferable to apply a cell adhesion inhibitor (cell adhesion-reducing agent).

Usable examples of cell adhesion inhibitors include phospholipid polymers, polyvinyl alcohol derivatives, phospholipid-polymer complexes, polyhydroxyethyl methacrylate, polyvinyl alcohol, agarose, chitosan, polyethylene glycol, albumin, and the like. These can be used in combination.

When the culture target 30 is spheres, the culture container of the present embodiment can be used, for example, in a step of sphere formation, a step of culture and growth while maintaining the sphere state, and a step of differentiation induction in the sphere state.

In addition, the culture container of the present embodiment can also be used, for example, in a method of forming spheres using differentiated cells obtained through a differentiation induction process from iPS cells, ES cells, or other stem cells, or a method of once cryopreserving differentiated cells, thawing them again, and then forming spheres.

Further, spheres formed to contain desired differentiation-inducing cells can be cleaned with a phosphate buffer or physiological saline, or suspended in water for injection, before administration to the living body.

Here, as the cleaning of spheres, after the formation of spheres in the culture container of the present embodiment, the spheres may be cleaned with a cleaning liquid fed in the culture container; or after the formation of spheres in another culture container, such as a bioreactor, the spheres may be transferred to the culture container of the present embodiment and cleaned in a state in which the spheres do not overlap each other.

In addition, as described above, it is also possible to perform cleaning when differentiated cells are once cryopreserved and thawed again, and then spheres are formed.

That is, differentiated cells induced by adherent culture or in the sphere state are not always administered immediately to the living body; they may be once cryopreserved and thawed before use.

Because of the nature of cells, it is difficult to freeze cells in the sphere state. Even if differentiation is induced in spheres, it is necessary to break them into single cells before freezing.

After the differentiated single cells are thawed, it is necessary to form spheres again for administration; however, before administration, it is necessary to clean the spheres to remove the medium in the sphere formation, debris, etc.

However, sphere cleaning is not only time-consuming, as described above, but also poses a risk of contamination because it is often performed in an open system. In addition, its quality control is also costly.

Since the use of the culture container of the present embodiment facilitates not only medium replacement but also sphere cleaning in sphere culture, it is very advantageous in sphere culture. For example, when spheres are mass-cultured in a bioreactor or the like, and frozen after being returned to single cells, it is easy to subsequently form and clean spheres, and then suspend them in water for injection for each dose using the culture container of the present embodiment.

Moreover, the culture container of the present embodiment can be particularly suitably used for a culture bag made of a flexible packaging material. This makes it possible to solve the problems of conventional culture bags having many recesses in their culture surface.

That is, in such a culture bag, when a medium is fed into the bag to replace the medium, the spheres easily pop out of the wells and move to other wells. Therefore, for example, in the case of a culture container with an outer diameter of 100 mm×50 mm having circular wells with a diameter of 1 mm and a depth of 0.5 mm, the medium could only be fed at a flow rate of about 0.2 ml/min.

In addition, in such a culture bag, the flow rate near the port is particularly higher, and the spheres near the port become easier to move. Therefore, in order to sufficiently prevent the movement of the spheres near the port, the medium could only be fed at a flow rate of about 0.02 ml/min in some cases.

In contrast, the culture container of the present embodiment can feed the medium without taking the flow rate into consideration; thus, the spheres can be cultured efficiently. For example, with the culture container of the present embodiment, the medium can be fed at a rate of 5 ml/min.

The culture container of the present embodiment is not limited to a culture bag made of a flexible packaging material, and can also be a dish-shaped rigid culture container.

Figure 3:
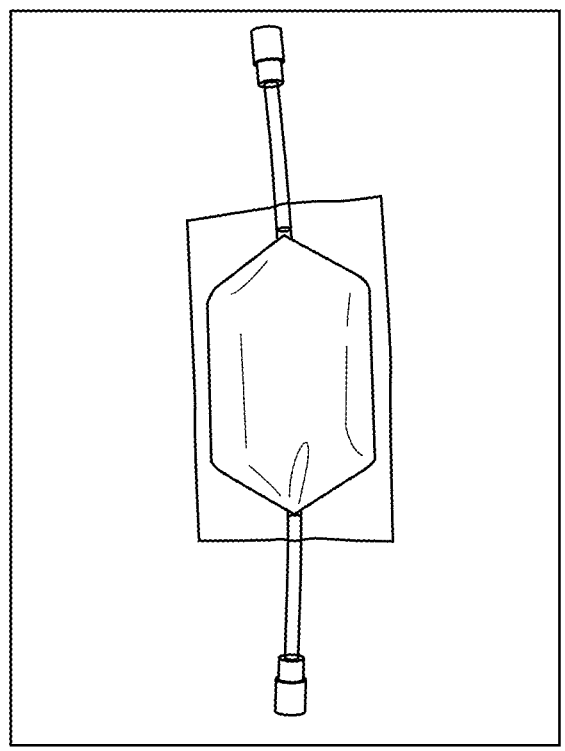
FIG. 3 is a picture of the entirety of a culture container produced as the culture container according to the first embodiment of the present invention.
Figure 4:
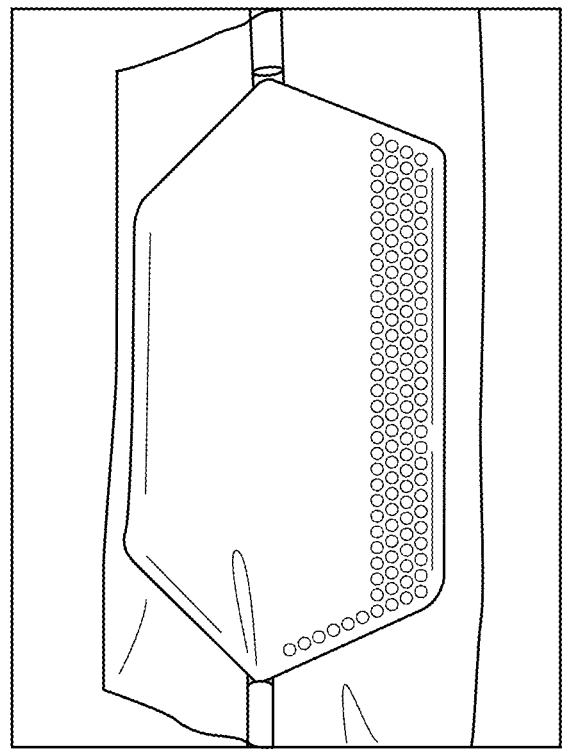
FIG. 4 is a picture of part of the culture container produced as the culture container according to the first embodiment of the present invention.

FIGS. 3 and 4 show photographs of a culture container produced as the culture container according to the present embodiment.

This culture container is made of polyethylene, and is formed by bonding a container body 10 and a top plate 20, each of which has a size of 12 cm×7 cm, by heat sealing. Ports are provided at both ends, the diameter of the recess is 2 mm, the height of the top plate protrusion portion is 50 μm, and the width of the top plate protrusion portion is 100 μm. In addition, the top plate protrusion portions are arranged at intervals of 2 mm so as to cover the entire culture surface.

In place of spheres, beads with a diameter of 200 m were placed in the recesses of this culture container, a medium was fed while the top plate was pressed against the container body. It was confirmed that the beads did not pop out of the recesses or move to the neighboring recesses.

Even when the culture container was inverted to discharge the entire medium from the recesses, the beads remained in the recesses.

Second Embodiment

Figure 5:
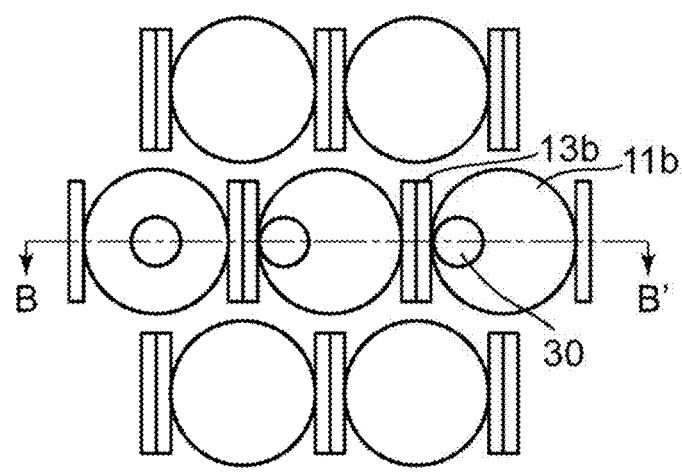
FIG. 5 shows a partially enlarged schematic plan view and a cross-sectional view of a culture container according to a second embodiment of the present invention.
Figure 5:
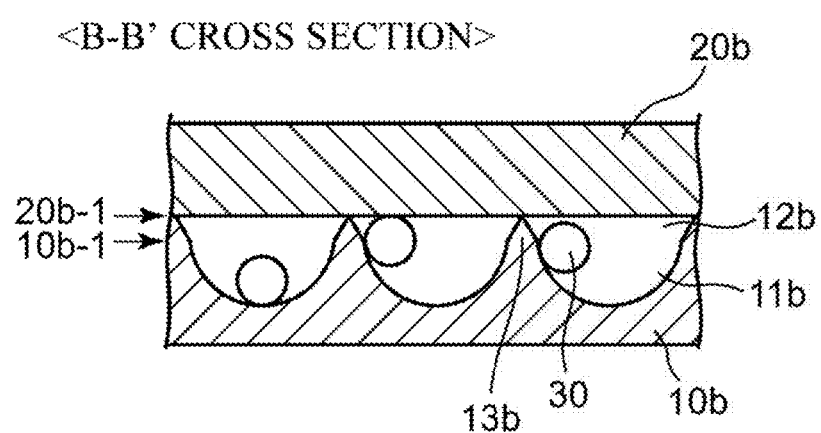

Next, the culture container, the culture method, and the transportation method according to the second embodiment of the present invention will be described with reference to FIG. 5. FIG. 5 shows a partially enlarged schematic plan view and a cross-sectional view of the culture container according to the present embodiment.

The culture container of the present embodiment is a culture container including a plurality of recesses for accommodating a culture target, and includes a container body 10b and a top plate 20b, as shown in FIG. 5.

The container body 10b has a first surface 10b-1 in which openings 12b of recesses 11b are formed, and the first surface 10b-1 and the surface that forms the side walls of the recesses 11b are used as a culture surface to configure the bottom of the culture container.

The top plate 20b has a second surface 20b-1 facing the first surface 10b-1 of the container body 10b.

That is, the first surface 10b-1 of the container body 10b and the second surface 20b-1 of the top plate 20b are disposed to face each other to form a culture container, and the container body 10b and the top plate 20b are partially in contact with each other to form a channel between the container body 10b and the top plate 20b. The width of the channel is smaller than the minimum diameter of a culture target 30.

Specifically, the culture container of the present embodiment includes body protrusion portions 13b on the first surface 10b-1 side of the container body 10b.

The height of the body protrusion portion 13b is smaller than the minimum diameter of the culture target 30.

Then, the tips of the body protrusion portions 13b are in contact with a part of the second surface 20b-1 of the top plate 20 to form a gap between the first surface 10b-1 of the container body 10b and the second surface 20b-1 of the top plate 20b.

FIG. 5 shows a schematic plan view illustrating a state in which spheres as the culture target 30 are accommodated in part of such a culture container, and a B-B' cross-sectional view.

In the B-B' cross-sectional view, the body protrusion portions 13b have a triangular prism shape protruding from the first surface 10-1, and are uniformly arranged between all of the recesses; however, the shape and arrangement of the body protrusion portions 13b are not limited thereto. Various shapes and arrangements can be employed within the range in which a gap can be formed between the first surface 10b-1 and the second surface 20b-1.

That is, the body protrusion portions 13b can have, for example, a semicircular cylindrical shape protruding from the first surface 10b-1, and can be arranged at random on the first surface 10b-1.

The gap between the first surface 10b-1 of the container body 10b and the second surface 20b-1 of the top plate 20b is the same as the height of the body protrusion portion 13b, and the height of the body protrusion portion 13b is smaller than the diameter of the culture target.

Therefore, the culture target cannot pass through the gap between the first surface 10b-1 and the second surface 20b-1, and can be retained in the recesses 11b.

The other configurations and effects of the culture container of the present embodiment are the same as those of the first embodiment.

Third Embodiment

Figure 6:
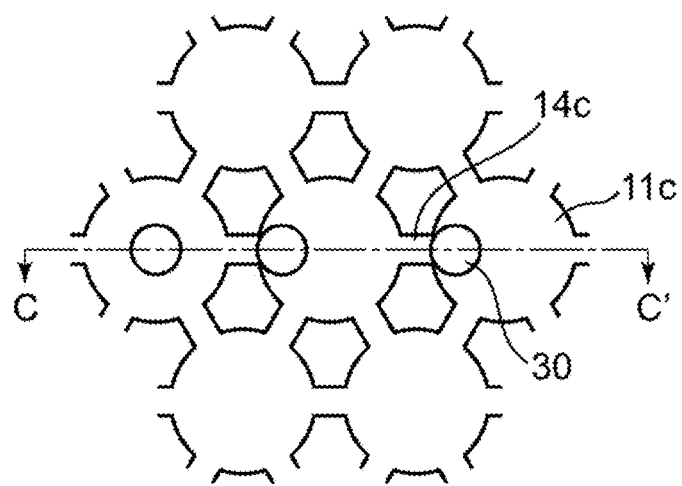
FIG. 6 shows a partially enlarged schematic plan view and a cross-sectional view of a culture container according to a third embodiment of the present invention.
Figure 6:
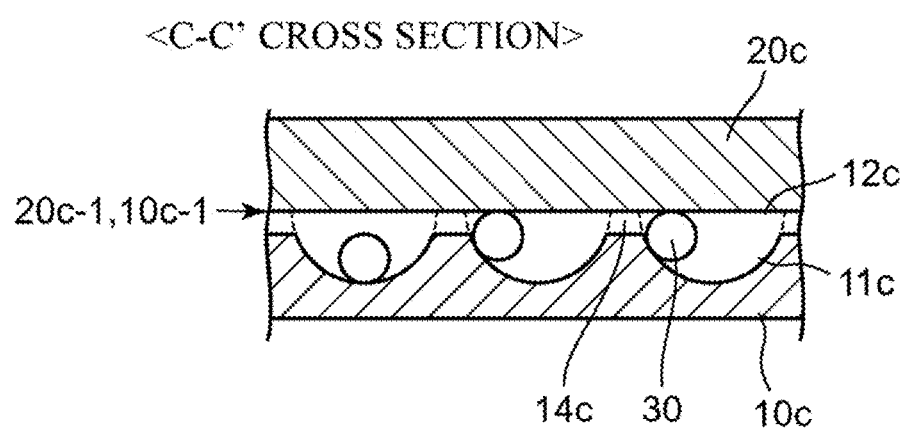

The culture container, the culture method, and the transportation method according to the third embodiment of the present invention will be described with reference to FIG. 6. FIG. 6 shows a partially enlarged schematic plan view and a cross-sectional view of the culture container according to the present embodiment.

The culture container of the present embodiment is a culture container including a plurality of recesses for accommodating a culture target, and includes a container body 10c and a top plate 20c, as shown in FIG. 6.

The container body 10c has a first surface 10c-1 in which openings 12c of recesses 11c are formed, and the first surface 10c-1 and the surface that forms the side walls of the recesses 11c are used as a culture surface to configure the bottom of the culture container.

The top plate 20c has a second surface 20c-1 facing the first surface 10c-1 of the container body 10c. In FIG. 6, these surfaces are partially in contact with each other.

That is, the first surface 10c-1 of the container body 10c and the second surface 20c-1 of the top plate 20c are disposed to face each other to form a culture container, and the container body 10c and the top plate 20c are partially in contact with each other to form a channel between the container body 10c and the top plate 20c. The width of the channel is smaller than the minimum diameter of a culture target 30.

Specifically, the culture container of the present embodiment includes body channel portions 14c on the first surface 10c-1 side of the container body 10c.

The body channel portions 14c are provided between the recesses 11c so as to connect all of the recesses 11c to one space.

The phrase "connect all of the recesses 11c to one space" means that while the first surface 10c-1 and the second surface 20c-1 are partially in contact with each other, all of the recess 11c form one space so that the medium can be fed into all of the recesses 11c. The same applies to the fourth embodiment.

The width of the body channel portion 14c is smaller than the minimum diameter of the culture target 30.

In the present embodiment, the first surface 10c-1 and the second surface 20c-1 are partially (other than regions corresponding to the openings 12c and the body channel portions 14c) in contact with each other to form the body channel portions 14c between the container body 10c and the top plate 20c.

FIG. 6 shows a schematic plan view illustrating a state in which spheres as the culture target 30 are accommodated in part of such a culture container, and a C-C' cross-sectional view.

In the C-C' cross-sectional view, the body channel portions 14c are formed in a substantially cylindrical shape uniformly between all of the recesses; however, the shape and arrangement of the body channel portions 14c are not limited thereto. Various shapes and arrangements can be employed within the range in which a channel can be formed between the container body 10c and the top plate 20c.

That is, the body channel portions 14c can have, for example, a prism shape, and can be arranged at random to connect all of the recesses 11c to one space.

In the present embodiment, the first surface 10c-1 and the second surface 20c-1 (other than regions corresponding to the openings 12c and the body channel portions 14c) are in contact with each other, and the width of the body channel portion 14c is smaller than the diameter of the culture target.

Therefore, the culture target cannot pass through the body channel portions 14c, and can be retained in the recesses 11c.

The other configurations and effects of the culture container of the present embodiment are the same as those of the first embodiment.

Fourth Embodiment

Figure 7:
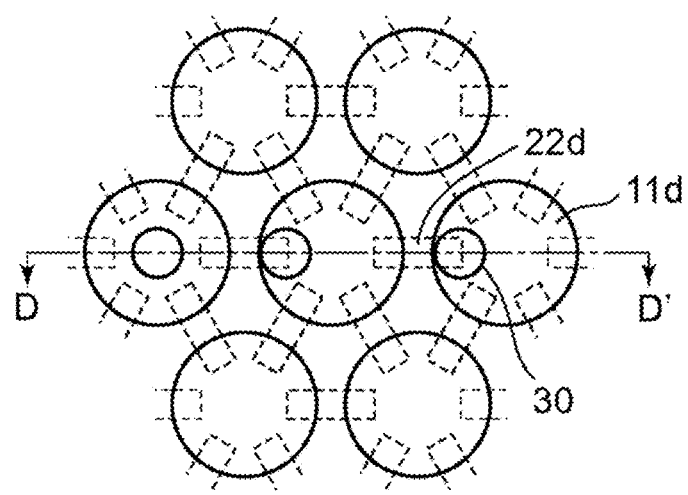
FIG. 7 shows a partially enlarged schematic plan view and a cross-sectional view of a culture container according to a fourth embodiment of the present invention.
Figure 7:
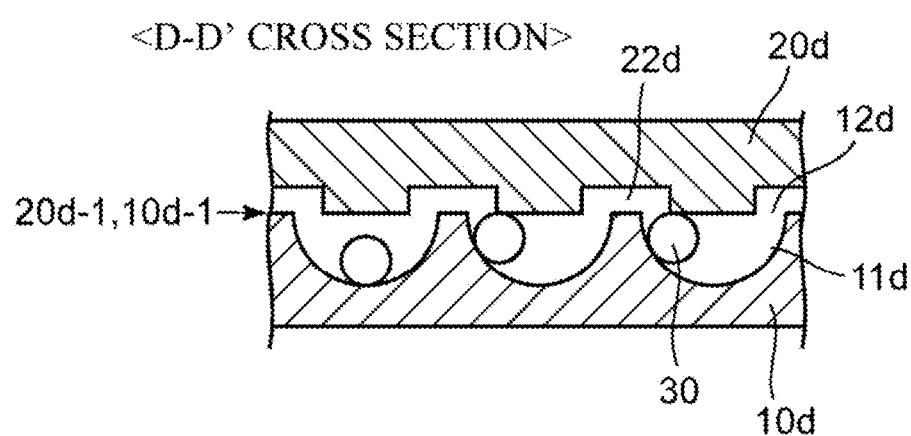

The culture container, the culture method, and the transportation method according to the fourth embodiment of the present invention will be described with reference to FIG. 7. FIG. 7 shows a partially enlarged schematic plan view and a cross-sectional view of the culture container according to the present embodiment.

The culture container of the present embodiment is a culture container including a plurality of recesses for accommodating a culture target, and includes a container body 10d and a top plate 20d, as shown in FIG. 7.

The container body 10d has a first surface 10d-1 in which openings 12d of recesses 11d are formed, and the first surface 10d-1 and the surface that forms the side walls of the recesses 11d are used as a culture surface to configure the bottom of the culture container.

The top plate 20d has a second surface 20d-1 facing the first surface 10d-1 of the container body 10d. In FIG. 7, these surfaces are partially in contact with each other.

That is, the first surface 10d-1 of the container body 10d and the second surface 20d-1 of the top plate 20d are disposed to face each other to form a culture container, and the container body 10d and the top plate 20d are partially in contact with each other to form a channel between the container body 10d and the top plate 20d. The width of the channel is smaller than the minimum diameter of a culture target 30.

Specifically, the culture container of the present embodiment includes top plate channel portions 22d on the second surface 20d-1 side of the top plate 20d.

The top plate channel portions 22d are provided on the top plate 20 so as to connect all of the recesses 11d to one space.

The width of the top plate channel portion 22d is smaller than the minimum diameter of the culture target 30.

In the present embodiment, the first surface 10d-1 and the second surface 20d-1 are partially (other than regions corresponding to the openings 12d and the top plate channel portions 22d) in contact with each other to form the top plate channel portions 22d between the container body 10d and the top plate 20d.

FIG. 7 shows a schematic plan view illustrating a state in which spheres as the culture target 30 are accommodated in part of such a culture container, and a D-D' cross-sectional view.

In the D-D' cross-sectional view, the top plate channel portions 22d have a substantially cylindrical shape, and are formed uniformly to connect all of the recesses; however, the shape and arrangement of the top plate channel portions 22d are not limited thereto. Various shapes and arrangements can be employed within the range in which a channel can be formed between the container body 10d and top plate 20d.

That is, the top plate channel portions 22d can have, for example, a prism shape, and can be arranged at random to connect all of the recesses 11d to one space.

In the present embodiment, the first surface 10d-1 and the second surface 20d-1 are partially (other than regions corresponding to the openings 12d and the top plate channel portions 22d) in contact with each other, and the width of the top plate channel portion 22d is smaller than the diameter of the culture target.

Therefore, the culture target cannot pass through the top plate channel portions 22d, and can be retained in the recesses 11d.

The other configurations and effects of the culture container of the present embodiment are the same as those of the first embodiment.

Further, it is also possible to combine the configurations of the culture containers of the first to fourth embodiments.

Specifically, the configurations of the culture containers of the first and second embodiments can be combined so that top plate protrusion portions are provided on the second surface, and body protrusion portions are provided between a plurality of recesses in the first surface.

In this case, the height of the top plate protrusion portion is the same as the height of the body protrusion portion, and a gap that is the same as the height of these portions and smaller than the minimum diameter of the culture target is formed between the first surface and the second surface.

Moreover, the configuration of the culture container of the first and/or second embodiment and the configuration of the culture container of the third embodiment can be combined so that at least either of top plate protrusion portions and body protrusion portions are provided, and body channel portions are provided in the first surface.

In this case, a gap is formed out of contact with the first surface and the second surface, and the sum of the width of the body channel portion and the width of the gap between the first surface and the second surface is smaller than the minimum diameter of the culture target.

In addition, the configuration of the culture container of the first and/or second embodiment and the configuration of the culture container of the fourth embodiment can be combined so that at least either of top plate protrusion portions and body protrusion portions are provided, and top plate channel portions are provided in the second surface.

In this case, a gap is formed out of contact with the first surface and the second surface, and the sum of the width of the top plate channel portion and the width of the gap between the first surface and the second surface is smaller than the minimum diameter of the culture target.

Further, the configurations of the culture containers of the third and fourth embodiments can be combined so that body channel portions and top plate channel portions are provided.

In this case, the first surface and the second surface are partially in contact with each other, and the sum of the width of the body channel portion and the width of the top plate channel portion is smaller than the minimum diameter of the culture target.

In addition, all of the configurations of the culture containers of the first to fourth embodiments can be combined.

In this case, the height of the top plate protrusion portion is the same as the height of the body protrusion portion, a gap is formed out of contact with the first surface and the second surface, and the sum of the width of the gap between the first surface and the second surface, the width of the body channel portion, and the width of the top plate channel portion is smaller than the minimum diameter of the culture target.

As explained above, according to the culture container, the culture method, and the transportation method according to embodiments of the present invention, in the culture container including a plurality of recesses for culturing a culture target, such as spheres, a liquid substance, such as a medium, can flow between the recesses, cells and debris smaller than the minimum diameter of the culture target can pass between the recesses, and the movement of the culture target between the recesses can be prevented.

The present invention is not limited to the above-mentioned embodiments, and it is needless to say that various modifications are possible within the scope of the present invention.

For example, the size of the culture container is not limited to the size shown in the embodiments, and can be suitably changed to a size that can form, for example, 500,000 to a million of spheres.

INDUSTRIAL APPLICABILITY

The present invention can be suitably used, for example, for efficiently mass-producing spheres with a uniform size arranged at regular intervals.

The documents described in the specification and the Japanese patent application claiming the priority under the Paris Convention to the invention are incorporated herein by reference in its entirety.

DESCRIPTION OF REFERENCE SIGNS 10, 10b, 10c, 10d: Container body
10-1, 10b-1, 10c-1, 10d-1: First surface
11, 11b, 11c, 11d: Recess
12, 12b, 12c, 12d: Opening
13b: Body protrusion portion
14c: Body channel portion
20, 20b, 20c, 20d: Top plate
20-1, 20b-1, 20c-1, 20d-1: Second surface
21: Top plate protrusion portion
22d: Top plate channel portion
30: Culture target

The invention claimed is:

1. A culture container comprising recesses and culture targets accommodated in the recesses, respectively, wherein
the culture container is a closed culture bag,
the culture container comprises a container body having a first surface in which the recesses are formed, and a top plate having a second surface facing the first surface,
the container body and the top plate are made of polyolefin resin that is a flexible packaging material,
top plate protrusion portions are provided on the second surface side, protruding to bottoms of the recesses, respectively,
a width of each of the top plate protrusion portions is smaller than a width of an opening of each of the recesses, and a length of each of the top plate protrusion portions, from a tip to a bottom thereof, is smaller than the minimum diameter of each of the culture targets,
a gap is formed between the first surface and the second surface,
the gap forms a channel for fluid between the container body and the top plate, and
a length of the gap in a direction along the length of protrusion portions at an outermost contour of each of the recesses is smaller than a minimum diameter of each of the culture targets, such that the culture targets are encased inside the recesses.

2. The culture container according to claim 1, wherein
body channel portions are provided on the first surface side,
the body channel portions are provided between the recesses to connect all of the recesses to one space,
a sum of a width of the body channel portion and a width of the gap between the first surface and the second surface is smaller than the minimum diameter of the culture target, and
the container body and the top plate are partially in contact with each other to form a channel between the container body and the top plate.

3. The culture container according to claim 1, wherein
top plate channel portions are provided on the second surface side,
the top plate channel portions are provided to connect all of the recesses to one space,
a sum of a width of the top plate channel portion and a width of the gap between the first surface and the second surface is smaller than the minimum diameter of the culture target, and
the container body and the top plate are partially in contact with each other to form a channel between the container body and the top plate.

4. The culture container according to claim 1, wherein the culture target is a cell, a sphere, an organoid, or a body tissue.

5. A culture method using the culture container according to claim 1, the method comprising
inserting and removing a medium or a cleaning liquid through the channel formed between the container body and the top plate.

6. The culture method according to claim 5, wherein the culture container containing a medium or a cleaning liquid is tilted or inverted to insert and remove the medium or the cleaning liquid through the channel.

7. A transportation method using the culture container according to claim 1, the method comprising
storing or transporting the culture target while accommodating the culture target in the recesses and filling the recesses and the channel formed between the container body and the top plate with a medium, a cleaning liquid, or a cell preservation liquid.

* * * * *